United States Patent [19]
Wagner et al.

[11] Patent Number: 6,095,817
[45] Date of Patent: *Aug. 1, 2000

[54] DENTAL IMPLANT HAVING MULTIPLE TEXTURED SURFACES

[75] Inventors: William R. Wagner, Escondido; Brooks Story, Carlsbad, both of Calif.

[73] Assignee: Sulzer Calcitek Inc., Carlsbad, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/256,879

[22] Filed: Feb. 24, 1999

Related U.S. Application Data

[63] Continuation-in-part of application No. 08/860,657, filed as application No. PCT/US95/16219, Dec. 8, 1995.

[51] Int. Cl.⁷ ..................................... A61C 8/00
[52] U.S. Cl. ........................... 433/173; 433/174
[58] Field of Search ................... 433/172, 173, 433/174, 175, 176, 201.1

[56] References Cited

U.S. PATENT DOCUMENTS

| | | |
|---|---|---|
| 3,797,113 | 3/1974 | Brainin . |
| 3,808,606 | 5/1974 | Tronzo . |
| 3,849,887 | 11/1974 | Brainin . |
| 3,855,638 | 12/1974 | Pilliar . |
| 3,934,347 | 1/1976 | Lash et al. . |
| 4,011,602 | 3/1997 | Rybicki et al. . |
| 4,206,516 | 6/1980 | Pilliar . |
| 4,252,525 | 2/1981 | Child . |
| 4,261,350 | 4/1981 | Branemark et al. . |
| 4,379,694 | 4/1983 | Riess . |
| 4,492,577 | 1/1985 | Farris et al. . |
| 4,531,916 | 7/1985 | Scantlebury et al. . |
| 4,542,539 | 9/1985 | Rowe Jr., et al. . |
| 4,712,681 | 12/1987 | Branemark et al. . |
| 4,728,331 | 3/1988 | Russier . |
| 4,767,328 | 8/1988 | Branemark . |
| 4,793,808 | 12/1988 | Kirsch . |
| 4,842,517 | 6/1989 | Kawahare et al. . |
| 4,850,870 | 7/1989 | Lazzara et al. . |
| 4,854,872 | 8/1989 | Detsch . |
| 4,854,873 | 8/1989 | Linden . |
| 4,872,840 | 10/1989 | Bori . |
| 4,881,897 | 11/1989 | Franek et al. . |
| 4,934,935 | 6/1990 | Edwards . |
| 4,957,819 | 9/1990 | Kawahara et al. . |
| 4,986,753 | 1/1991 | Sellers . |
| 5,002,488 | 3/1991 | Homsy . |
| 5,049,074 | 9/1991 | Otani et al. . |
| 5,104,410 | 4/1992 | Chowdhary . |
| 5,110,292 | 5/1992 | Balfour et al. . |
| 5,195,891 | 3/1993 | Sule . |
| 5,209,659 | 5/1993 | Friedman et al. . |
| 5,263,986 | 11/1993 | Noiles et al. . |
| 5,310,343 | 5/1994 | Hasegawa et al. ................ 433/173 |
| 5,312,256 | 5/1994 | Scortecci ...................... 433/173 X |
| 5,316,476 | 5/1994 | Krauser .......................... 433/173 |
| 5,344,457 | 9/1994 | Pilliar et al. . |
| 5,360,448 | 11/1994 | Thramann . |
| 5,492,470 | 2/1996 | Anders . |
| 5,564,923 | 10/1996 | Grassi et al. ................... 433/173 |
| 5,571,017 | 11/1996 | Niznick ........................ 433/173 X |
| 5,571,617 | 11/1996 | Cooprider et al. . |
| 5,636,989 | 6/1997 | Somborac et al. ............... 433/173 |
| 5,639,237 | 6/1997 | Fontenot ........................ 433/173 |
| 5,863,201 | 1/1999 | Lazzara et al. ................ 433/173 X |
| 5,885,079 | 3/1999 | Niznick . |

OTHER PUBLICATIONS

M. Block, et al., "Loaded Hydroxylapatite–Coated and Grit–Blasted Titanium Implants in Dogs," The International Journal of Oral & Maxillofacial Implants, (1989), vol. 4, pp. 219–225.

D. Buser, et al., Influence of Surface Characteristsics on Bone Integration of Titanium Implants.

A Histomorphometric Study in Miniature Pigs, Journal of Biomedical Materials Research, (1991), vol. 25, pp. 889–902.

*Primary Examiner*—Nicholas D. Lucchesi
*Attorney, Agent, or Firm*—Philip S. Lyren; Kenneth S. Barrow

[57] ABSTRACT

A dental implant for osseointegration in alveolar bone. The implant includes at least three different and distinct surface regions.

7 Claims, 6 Drawing Sheets

DENTAL IMPLANT HAVING MULTIPLE TEXTURED SURFACES

"This is a continuation-in-part of U.S. application Ser. No. 08/860,657 filed on Oct. 2, 1997 entitled "Dental Implant Having Multiple Textured Surfaces" which claims priority under PCT application Ser. No. PCT/US95/16219 filed on Dec. 8, 1995."

TECHNICAL FIELD

The present invention relates generally to a dental implant for osseointegration in alveolar bone, with the implant configured to receive an abutment for supporting a dental prosthesis.

BACKGROUND ART

One known arrangement for a dental implant involves an implant portion, or artificial root, that is received in a hole prepared in alveolar bone, and an abutment, or prosthesis support, that is securable to the implant portion and that extends beyond the gingival tissue to support a tooth prosthesis. The implant portion and the abutment are constructed as separate components that are secured together by means of a screw passed through the abutment and received within a threaded bore in the implant portion.

In a first surgical procedure, an incision is made in the gingival tissue to expose the alveolar bone. Following any dressing of the surface of the bone that may be necessary, a hole that is complementary in shape to the implant portion is drilled in the bone and the implant portion is inserted. A healing cap or screw is attached to the implant portion to occlude the threaded bore, and the gingival tissue is stitched closed over the implant portion to await osseointegration.

In a subsequent second surgical procedure, following osseointegration of the implant portion, the gingival tissue is again opened to expose the implant portion. The healing cap or screw is removed and replaced with a second healing cap having an outer surface corresponding in shape below the gum-line to that of the abutment, but protruding slightly above the gingival tissue. The gingival tissue surrounding the second healing cap is sutured thereabout to await healing in conformity to the outer surface of the second healing cap.

After the gingival tissue has healed, the second healing cap is removed and replaced with a permanent abutment that is secured to the implant. The abutment can be configured to support a single-tooth prosthesis fashioned thereon or to support a bridge structure carrying multiple tooth prostheses.

A common clinical problem associated with dental implants is loss of supporting bone at the coronal aspect of the implant. Such loss of bone can be caused by, among other things, infectious etiologies similar to those encountered in periodontal diseases of natural teeth. The association of periodontal pathogenic organisms with the loss of supporting alveolar bone highlights the need for scrupulous oral hygiene on the part of the patient and for the ability of a clinician to adequately prevent disease and to treat diseased implant sites. A smooth surface at the coronal end of a dental implant is more easily cleaned of plaque, pathogenic organisms, and endotoxins than is a rough surface that has crevices that cannot be reached readily by mechanical devices such as brushes. A smooth surface at the coronal end of an implant also facilitates increased accuracy of fit at the interface between the implant and the attached abutment, an important consideration since gaps between these components can harbor pathogenic accumulations, potentially leading to adverse clinical conditions. Consequently, dental implants with a smooth surface in the coronal region are commonly used in clinical practice.

Bone tissue reacts differently to metal surfaces with differing surface characteristics. Buser et al. (J Biomed Mater Res 25: 889–902, 1991) implanted cylindrical titanium implants having different surface characteristics in miniature pigs. They reported that the percentage of implant surface in direct contact with bone varied directly with increasing roughness of the titanium surface. It has also been observed by others that bone often does not attach to the smooth surface in the coronal region of dental implants. Rather, remodeling of the bone occurs such that the coronal attachment of bone is lowered to the first roughened or textured surface encountered.

To enhance osseointegration of dental implants, it has been proposed to provide a porous surface on the bone-engaging portion of the implant to permit ingrowth of bone into the surface of the implant. Such a porous surface can be provided on a metal implant by a coating of sintered metal powder, beads, or wire mesh, for example. Concerns have been expressed by some persons, however, that exposure of the porous surface of a dental implant to the oral cavity can result in apical migration of bacteria from the oral cavity through the pores of the porous surface, leading to infection of the bone and consequent loss of bony support for the implant. With that concern in mind, a porous coated dental implant is shown in U.S. Pat. No. 5,344,457, to Pilliar et al. wherein the implant includes a lower bone-engaging region coated with a porous surface into which bone may grow, and an upper bone-engaging region coated with a non-porous, relatively smooth, bioreactive surface (such as hydroxylapatite) to which bone can bond directly. The presence of bone in apposition to the implant surface above the level of the porous surface is said to afford protection of the porous surface from the migration of pathogens from the oral cavity.

It would be desirable to have an implant that offers optimum anchoring in bone by ingrowth of bone into a porous surface, a coronal surface designed for optimum hygiene, and protection of the porous surface from the oral cavity not afforded by smooth coronal surfaces. This and other desirable advantages are provided by the present invention.

SUMMARY

One aspect of the present invention involves a dental implant for osseointegration in alveolar bone of the type including an elongate body having a coronal end for engaging an abutment to which a tooth prosthesis can be attached. The elongate body has a bone-engaging surface including a first surface region in which the bone-engaging surface is sufficiently porous to permit ingrowth of bone therein. The bone-engaging surface further includes a second surface region in which the bone-engaging surface is non-porous, biocompatible metal that is sufficiently rough to permit bone to attach thereto. The second surface region is disposed intermediate the first surface region and the coronal end. The bone-engaging surface further includes a third surface region in which the bone-engaging surface is non-porous, biocompatible metal and is substantially smooth. The third surface region is disposed intermediate the second surface region and the coronal end.

It is an object of the present invention to provide a dental implant of the type having a porous surface to promote osseointegration, wherein the porous surface is protected from the oral cavity, and wherein good oral hygiene is facilitated at the coronal end of the implant.

Other objects and advantages of the present invention will be apparent from the following description of preferred embodiments of the invention made with reference to the drawings.

BEST MODE FOR CARRYING OUT THE INVENTION

Figure 1:
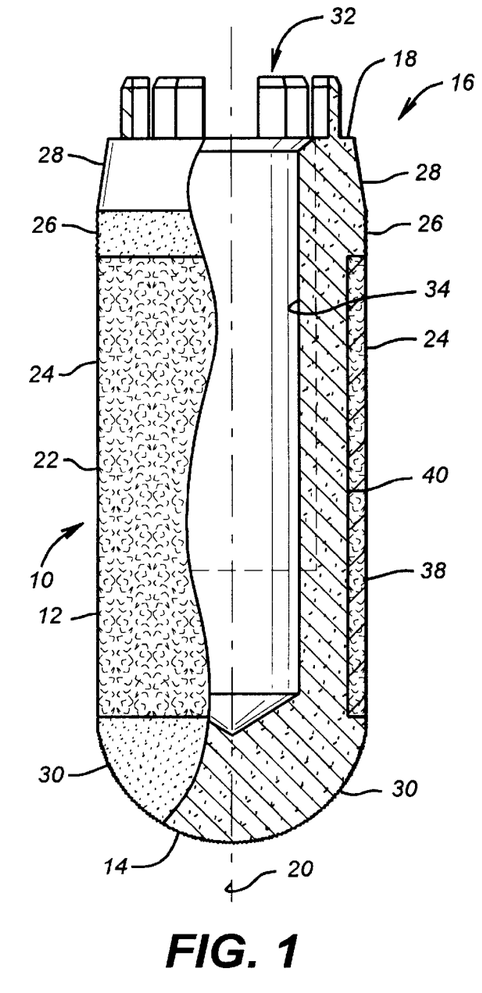
FIG. 1 is a side view, shown partially in cross-section, of a first embodiment of an implant useful for osseointegration within alveolar bone, with the cross-section taken along a plane including the longitudinal axis of the implant, and showing multiple textured surfaces.
Figure 2:
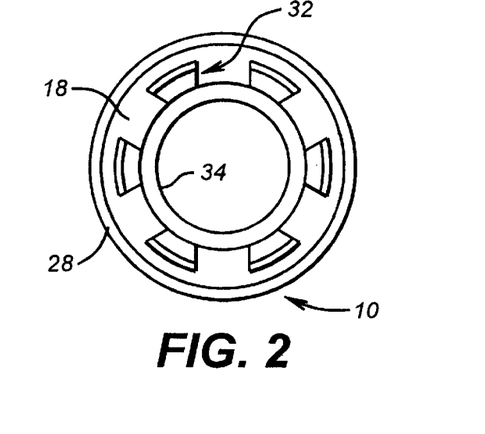
FIG. 2 is an end view of the implant of FIG. 1 showing the abutment-engaging end of the implant.

Referring to FIGS. 1 and 2, there is illustrated an implant 10 comprising part of a dental implant assembly and configured in accordance with the present invention. Implant 10 is preferably constructed of a biocompatible material such as titanium, and includes an elongate cylindrical body 12 having a proximal, or apical, end 14 and a distal, or coronal, end 16. As used throughout this description, the terms proximal and apical refer to that end or direction that is toward alveolar bone when the dental implant is implanted, and the terms distal and coronal refer to that end or direction that is away from alveolar bone and toward the oral cavity when the dental implant is implanted. Proximal end 14 is smoothly rounded and approximately hemispherical. Distal end 16, which may also be referred to as the abutment-engaging end for reasons that will become apparent from the description below, includes an annular shoulder 18 that extends to the periphery of cylindrical body 12 and lies in a plane perpendicular to the longitudinal axis 20 of cylindrical body 12. Cylindrical body 12 has a bone-engaging surface 22 with multiple textured surface regions 24, 26, 28 and 30. Region 28 tapers radially outwardly in the apical direction.

A plurality of splines 32 rise from and extend axially away from shoulder 18 in the distal direction. Splines 32 are interdigitated with similar splines on the proximal end of a mating abutment to provide anti-rotational engagement between the implant and abutment, and tactile feedback that signals full engagement between the implant and abutment, as is more fully described in U.S. Pat. No. 5,449,291, the disclosure of which is hereby incorporated by reference. A central coaxial threaded cylindrical bore 34 in cylindrical body 12 is open at distal end 16 for receiving a threaded screw to retain an abutment on implant 10.

A first surface region 24 of bone-engaging surface 22 is sufficiently porous to permit ingrowth of bone therein. By "porous," it is meant that the material underlying the surface is permeated with interconnected, randomly shaped pores that communicate with the surface. Surface 22 in first surface region 24 is comprised of a porous metal coating formed by sintering titanium or titanium alloy powder within recesses machined into the solid titanium or titanium alloy substrate of which elongate body 12 is constructed. Examples of other processes that are known in the art and that are believed to provide a suitable porous coating in first surface region 24 include sintering of metal beads or metal wire mesh to a titanium or titanium alloy substrate. Examples of specific processes for forming porous coatings are provided in U.S. Pat. Nos. 3,855,638; 4,206,516; 4,542,539; and 5,049,074.

A second surface region 26 of bone-engaging surface 22 is contiguous with and adjacent surface region 24 and is located intermediate region 24 and region 28. Surface 22 in region 26 is comprised of non-porous, biocompatible metal that is sufficiently rough to permit bone to attach thereto. Preferably, surface region 26 is formed by grit-blasting a previously machined surface of the solid titanium or titanium alloy of which elongate body 12 is constructed. Grit blasting at a distance of six to twenty inches with 60 grit alumina particles delivered through a ¼ inch nozzle by compressed air at 60 psi results in a rough, but non-porous, metal surface having an average surface roughness of about 127 microinches. Preferably, the average surface roughness should be in the range of about 75 to about 300 microinches to be sufficiently rough to promote bone attachment thereto. Growth and attachment of bone to surface 22 in region 26 results in a bone-to-implant seal that isolates and protects porous region 24 from exposure to the oral cavity. Region 26 is an annular band having a width along the longitudinal axis of elongate body 12 of about 0.25 mm to 2.00 mm, preferably about 0.50 mm to about 1.00 mm and most preferably about 0.75 mm.

Bone-engaging surface 22 also includes a third surface region 28, contiguous with and adjacent to surface region 26 and located intermediate region 26 and coronal end 16. Surface 22 in region 28 is comprised of non-porous, biocompatible metal that is substantially smooth. Surface region 28 is formed by machining the solid titanium or titanium alloy of which elongate body 12 is constructed. Surface 22 in region 28 should be sufficiently smooth to allow ready removal of bacterial plaque deposits thereon by conventional oral hygiene techniques, in the event that surface 22 in region 28 becomes exposed to the oral cavity. A sufficiently smooth machined surface, having an average surface roughness of about 32 microinches or less, can be provided by conventional machining processes. Region 28 is an annular band having a width along the longitudinal axis of elongate body 12 of about 0.25 mm to about 2.00 mm, preferably about 0.50 mm to about 1.00 mm and most preferably about 0.75 mm. Leaving surface 22 substantially smooth in region 28 also maintains sharp definition of shoulder 18 and permits a close fit to be maintained between implant 10 and the aforementioned abutment of the implant assembly, thereby enhancing the appearance of the prosthesis assembly when implanted and alleviating entrapment of bacteria at the implant-to-abutment interface.

Surface 22 in region 28 is shown tapered to provide a diametric transition between annular shoulder 18 and the maximum diameter of implant 12 that occurs in regions 24 and 26. The radially outward and apical taper of surface 22 in region 28 allows an implant of increased nominal diameter to be used with an abutment dimensioned to fit annular shoulder 18. Alternatively, the nominal diameter of the implant could correspond to that of annular shoulder 18, resulting in an implant of substantially constant diameter throughout regions 24, 26 and 28.

Referring again to FIG. 1, there is illustrated the porous metal coating 38 that comprises surface 22 in first surface region 24. Coating 38 is comprised of titanium metallic particles deposited into trough or recess 40 and sintered in place using any suitable sintering process as may be known in the art. Prior to the sintering step, cylindrical body 12, including trough 40 and splines 32, is machined from solid metal stock. Subsequently, coronal splines 32 and surface region 28 are masked. Cylindrical body 12 is then exposed to a grit blasting operation which creates the appropriate surface texture for exposed second surface region 26 and exposed surface region 30 at apical end 14, and creates a roughened surface in trough 40 which can enhance the strength of adhesion of coating 38 thereto during the sintering process. Masked surface region 28 and masked splines 32 are shielded from the grit blast, and retain their smooth machined surfaces.

Figure 3:
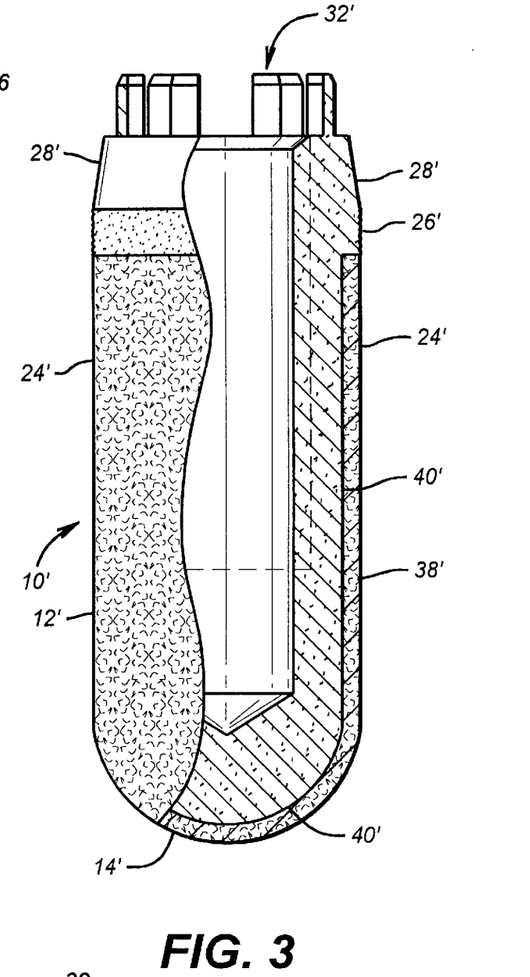
FIG. 3 is a side-view, shown partially in cross-section, of a second embodiment of an implant useful for osseointegration within alveolar bone, in which structures corresponding to the embodiment of FIGS. 1 and 2 are indicated by like primed reference numerals, and showing an alternate porous coating configuration.

FIG. 3 illustrates a further embodiment, in which trough 40' is similar to trough 40, but is extended to include the extreme apical hemispherical end 14'. In this embodiment, coating 38' covers the entire surface of elongate cylindrical body 12' apically of second surface region 26'.

Figure 4:
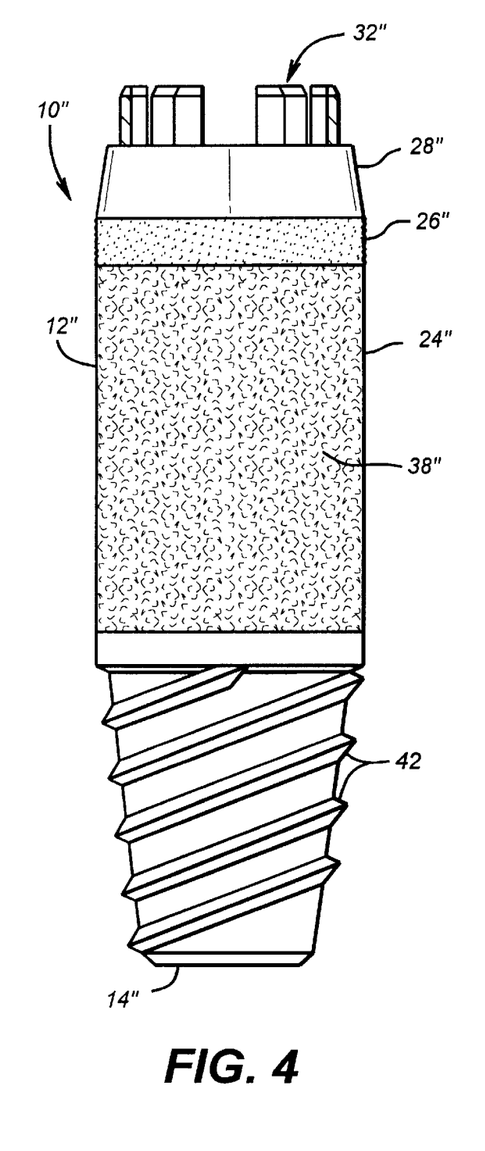
FIG. 4 is a side view of a third embodiment of an implant useful for osseointegration within alveolar bone, in which structures corresponding to the embodiment of FIGS. 1 and 2 are indicated by like double-primed reference numerals, and showing an alternate apical end configuration with a machined thread structure.

FIG. 4 illustrates a further embodiment in which the hemispherical apical end 14 of FIG. 1 is replaced by helical threads 42, machined into the metal of which implant body 12" is constructed, which threads allow the implant to be screwed into and mechanically anchored in bone at the time of surgical placement.

Figure 5:
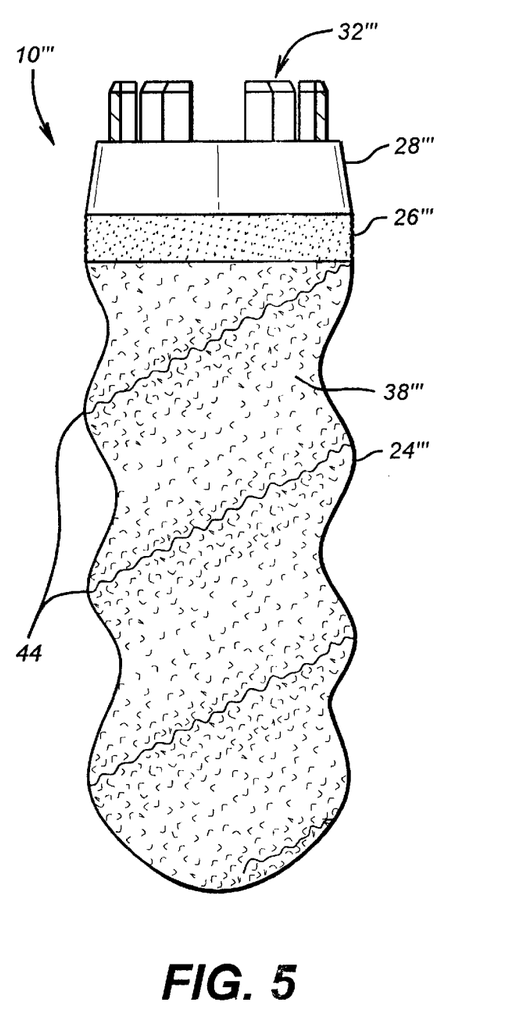
FIG. 5 is a side view of a fourth embodiment of an implant useful for osseointegration within alveolar bone, in which structures corresponding to the embodiment of FIGS. 1 and 2 are indicated by like triple-primed reference numerals, and showing an alternate macro-textured porous surface region having a thread-like macrotexture.

FIG. 5 illustrates a further embodiment in which the porous coating 38'" of first surface region 24'" is fashioned with a macrotexture, in the form of a thread 44. Other macrotextures, including concave and convex features such as dimples, grooves, or ridges are also contemplated.

Figure 6A:
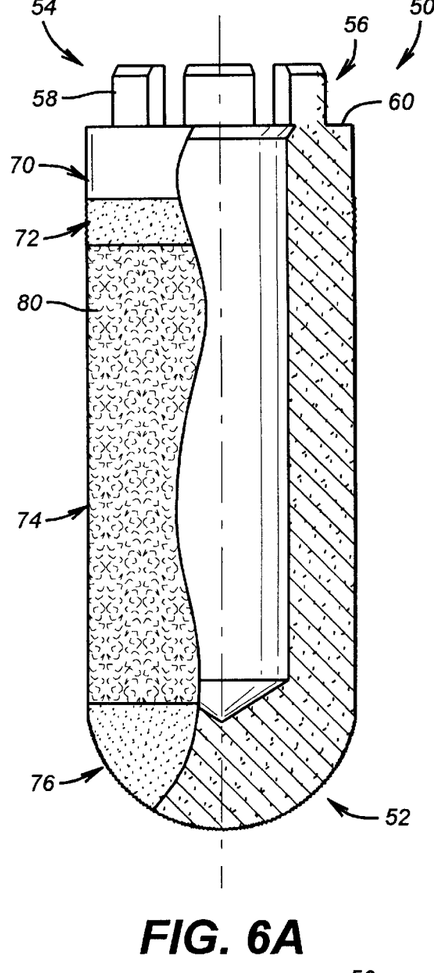
FIG. 6A is a side view of a fifth embodiment of an implant of the present invention.
Figure 6B:
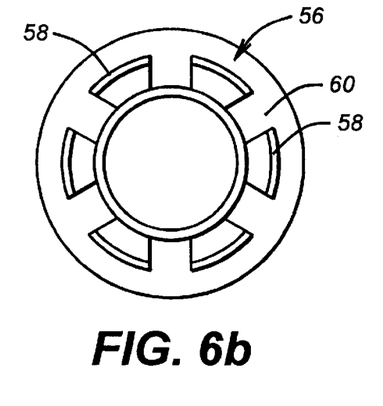
FIG. 6B is a top view of the implant of FIG. 6A.

FIGS. 6A, 6B, 7A, and 7B show two other alternate embodiments for the present invention. Each implant 50 includes a generally cylindrical body extending from a apical end 52 to a coronal end 54. The coronal end includes an engaging interface 56. In FIGS. 6A and 6B, the interface 56 includes a plurality of splines 58 that extend outwardly from a top surface 60. These splines are similar to those described in connection with FIGS. I and 2.

Figure 7A:
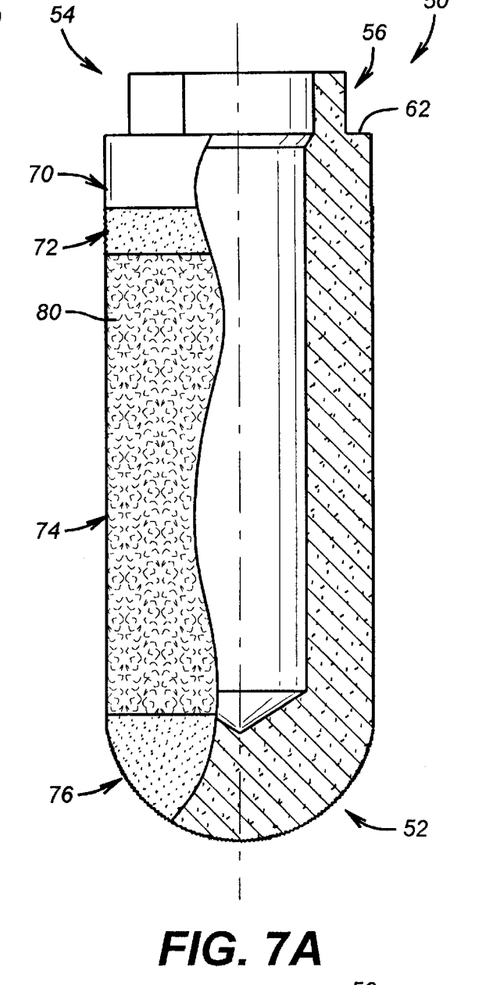
FIG. 7A is a side view of a sixth embodiment of an implant of the present invention.
Figure 7B:
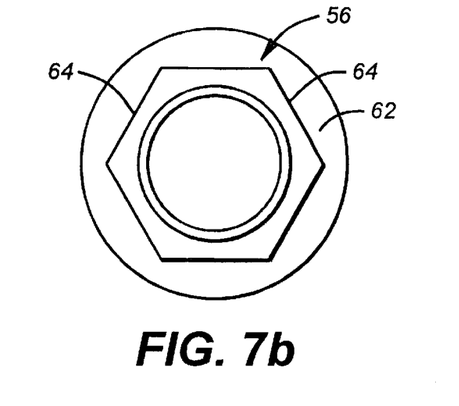
FIG. 7B is a top view of the implant of FIG. 7A.

In FIGS. 7A and 7B, the interface 56 is a hexagonal projection that extends upwardly from a top surface 62. As shown best in FIG. 7B, this hexagonal projection includes six flat surfaces 64.

Turning back now to FIGS. 6A and 7A, each implant 50 has four different and distinct surface regions, numbered 70, 72, 74, and 76.

Region 70 is contiguous with and adjacent to the engaging interface 56. This region is similar to region 28 described in connection with FIG. 1: although region 70 does not include a slight taper away from top surfaces 60 and 62.

Region 72 is adjacent to region 70. This region 72 is similar to region 26 described in connection with FIG. 1.

As shown in FIGS. 6A and 7A, region 74 extends along a substantial portion of the body of the implant 50. This region has a surface that is coated with a biocompatible material 80. This material 80 is a calcium phosphate and preferably is hydroxylapatite (HA). This material may also comprise plasma spray titanium. Alternatively, this region 74 may be left uncoated and the substrate textured using, for example, a grit blasting technique or other known roughening technique.

HA may be applied to region 74 in a variety of methods known to those skilled in the art. In a preferred method, the outer surface of region 74 is roughened, for example with grit blasting. The outer surface, for example, may be blasted with HA powder as the blast media to create the desired roughened surface. Typically, the desired roughness is about 30 to 60 microinches, as measured with a stylus-based surface profilometer.

Alternative blast media besides HA may also be used. These media include calcium carbonate, sodium bicarbonate or other blast media that can be dissolved readily in a solution, typically an acidic solution. In yet other alternate embodiments, the roughened surface can be created by a chemical etch method, such as acid etching. In still yet other embodiments, aluminum oxide or alumina ($Al_2O_3$) may be used to grit blast the implant bodies.

Once the outer surface of region 74 is roughened, the residual HA powder is removed. To remove this residual HA, the implant is rinsed in a solution of 5% hydrochloric acid. Thoroughly rinsing the implant in the hydrochloric acid solution fully removes all particles of the blast media to permit application of the HA coating without reducing the bond strength between the HA coating and the titanium substrate.

Once the implant is thoroughly rinsed, the HA coating is applied to region 74. Preferably, the HA coating is applied by plasma spraying, as known to those of ordinary skill in the art. During the plasma spraying process, a stream of mixed gases pass through a high temperature electric arc. The electric arc ionizes the gases into a plasma flame, and crystalline HA feedstock powder is fed into the stream of mixed gases. The heat at least partially melts the HA feedstock powder which is propelled at a relatively high velocity against the outer surface of implant. The molten particles of HA powder impinge against the outer surface 74 and rigorously adhere to the particulate-free surface to form a relatively thin coating of HA.

After the HA coating is applied to region 74, the implant may be further processed to increase the crystallinity of the HA. A preferred method of increasing the crystalline HA content is described in U.S. Pat. No. 5,730,598, issued on Mar. 24, 1998, which is incorporated herein by reference.

Region 76 is adjacent to region 74 and is formed along the apical end of the implant. This region 72 is similar to region 30 described in connection with FIG. 1.

Figure 8:
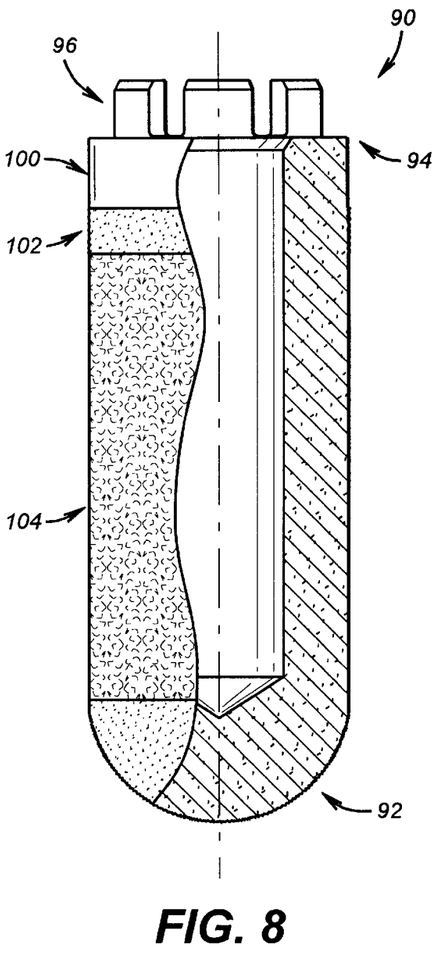
FIG. 8 is a side view of a seventh embodiment of an implant of the present invention.
Figure 9:
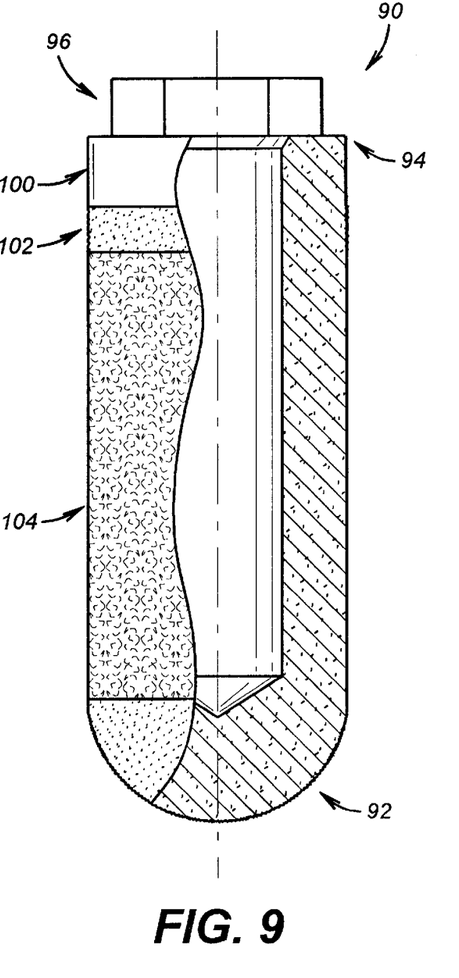
FIG. 9 is a side view of an eighth embodiment of an implant of the present invention.

FIGS. 8 and 9 show two other alternate embodiments for the present invention. Each implant 90 includes a generally cylindrical body extending from a apical end 92 to a coronal end 94. The coronal ends of FIGS. 8 and 9 include an engaging interface 96 that is similar to the engaging interface 56 described in connection with FIGS. 6A and 7A.

In FIGS. 8 and 9, each implant 90 has three different and distinct surface regions, numbered 100, 102, and 104.

Region 100 is contiguous with and adjacent to the engaging interface 96. This region is similar to region 28 described in connection with FIG. 1; although region 100 does not have a taper.

Region 102 is adjacent to region 100. This region 102 is similar to region 26 described in connection with FIG. 1.

Region 104 is adjacent to region 102 and is similar to region 74 described in connection with FIGS. 6A and 7A. Region 104, though, extends to the end of the implant to include the entire apical end 92.

Figure 10:
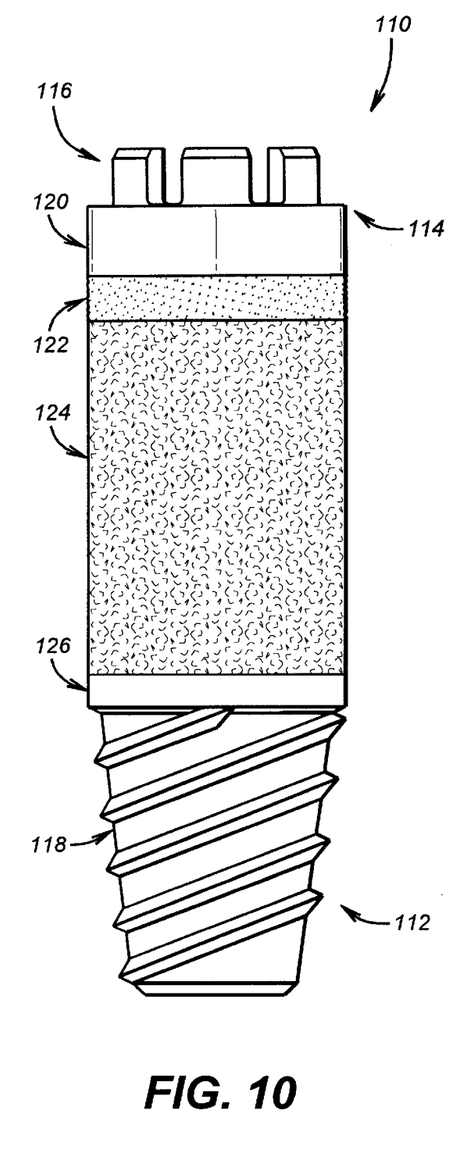
FIG. 10 is a side view of a ninth embodiment of an implant of the present invention.
Figure 11:
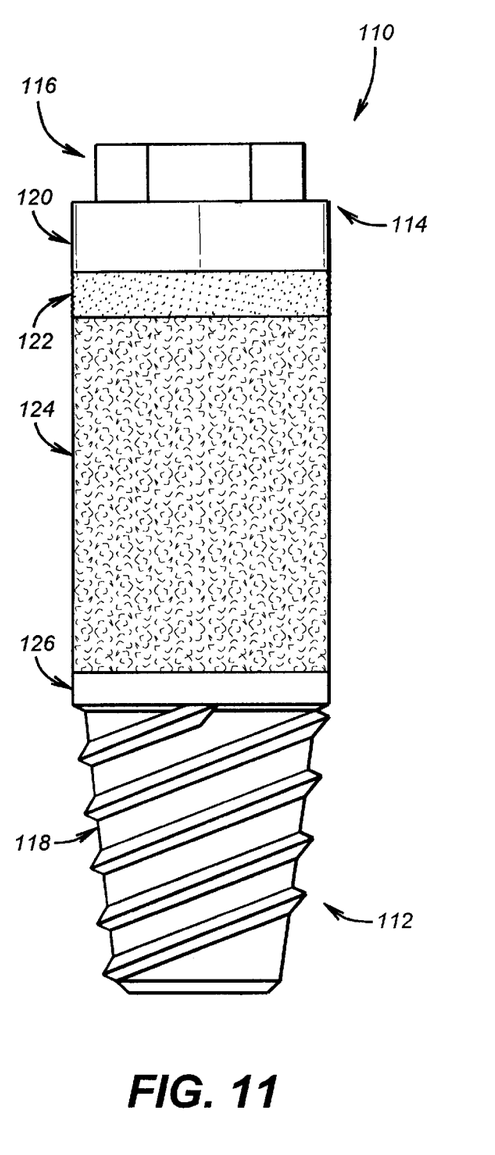
FIG. 11 is a side view of a tenth embodiment of an implant of the present invention.

FIGS. 10 and 11 show two other alternate embodiments for the present invention. Each implant 110 includes a generally cylindrical body extending from a apical end 112 to a coronal end 114. The coronal ends of FIGS. 10 and 11 include an engaging interface 116 that is similar to the engaging interface 56 described in connection with FIGS. 6A and 7A. The apical ends of FIGS. 10 and 11 also include an externally threaded portion 118.

In FIGS. 10 and 11, each implant 110 has four different and distinct surface regions, numbered 120, 122, 124, and 126.

Region 120 is contiguous with and adjacent to the engaging interface 116. This region is similar to region 28 described in connection with FIG. 1; although region 120 does not include a taper.

Region 122 is adjacent to region 120 is similar to region 26 described in connection with FIG. 1.

Region 124 is adjacent to region 122 and is similar to region 74 described in connection with FIGS. 6A and 7A.

Region 126 is adjacent to region 124 and is similar to region 42 described in FIG. 4.

Figure 12:
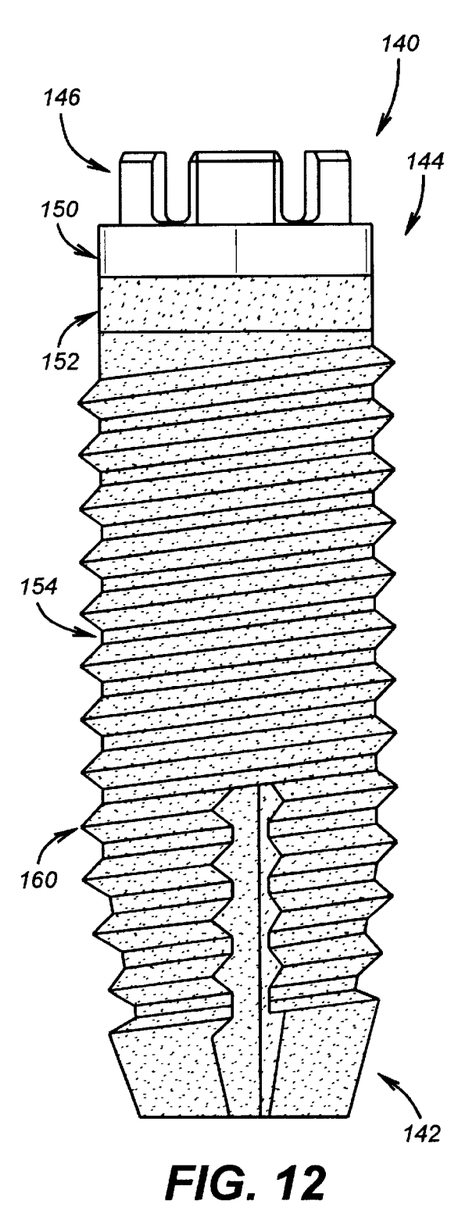
FIG. 12 is a side view of a eleventh embodiment of an implant of the present invention.
Figure 13:
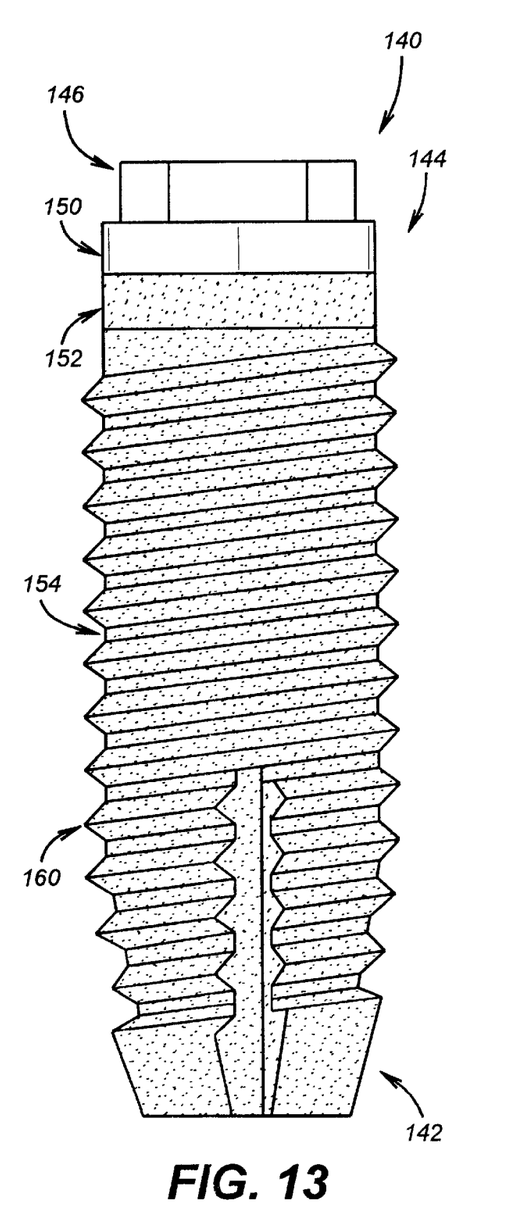
FIG. 13 is a side view of a twelfth embodiment of an implant of the present invention.

Turning now to FIGS. 12 and 13, two other alternate embodiments for the present invention are shown. Each implant 140 includes a generally cylindrical body extending from a apical end 142 to a coronal end 144. The coronal ends of FIGS. 12 and 13 include an engaging interface 146 that is similar to the engaging interface 56 described in connection with FIGS. 6A and 7A.

In FIGS. 12 and 13, each implant 140 has three different and distinct surface regions, numbered 150, 152, and 154.

Region 150 is contiguous with and adjacent to the engaging interface 146. This region is similar to region 28 described in connection with FIG. 1; although region 150 does not include a taper.

Region 152 is adjacent to region 150 is similar to region 26 described in FIG. 1.

Region 154 is adjacent to region 152 and is similar to region 74 described in FIGS. 6A and 7A. As shown in FIGS. 12 and 13, a substantial portion of the body of the implant includes external threads 160. These threads extend from region 152 to apical end 142. Further, the apical ends 142 also include a tapping channel 162.

It will be appreciated that the engaging interface shown in all of the figures may have any one of various configurations known to those skilled in the art. For example, the engaging interface may be another type of polygonal projection, such as an octagon, pentagon, or star. Further, the figures show a male type projection extending upwardly from the coronal end. The male projection though can instead be a female type connection, such as hexagonal or octagonal recess located at the coronal end. Variations on the type of engaging interface will not depart from the inventive aspect of this invention.

While the present invention has been illustrated and described with particularity in terms of preferred embodiments, it should be understood that no limitation of the scope of the invention is intended thereby. The scope of the invention is defined only by the claims appended hereto.

The invention claimed is:

1. A dental implant having an elongate body with a coronal end and an apical end, the implant comprising:
    a bone engaging surface having four separate and distinct regions, including:
        a first region adjacent said coronal end and having a substantially smooth surface;
        a second region adjacent the first region and having a substantially rough surface;
        a third region adjacent the second region and having a surface coated with hydroxylapatite; and
        a fourth region adjacent the third region and having a surface different than the third region.

2. The dental implant of claim 1 in which the fourth region has a substantially rough surface and has a non-threaded cylindrical configuration.

3. The dental implant of claim 1 in which the fourth region has a substantially smooth surface and has external threads extending to include the apical end.

4. A dental implant having an elongate body with a coronal end and a apical end, the implant comprising:
    a bone engaging surface having three separate and distinct regions, including:
        a first region adjacent said coronal end and having a substantially smooth surface;
        a second region adjacent the first region and having a substantially rough surface; and
        a third region adjacent the second region and having a surface coated with hydroxylapatite.

5. The dental implant of em 4 in which the third region includes external threads that extend substantially an entire length of the implant.

6. The dental implant of claim 4 in which the third region has a non-threaded configuration.

7. The dental implant of claim 4 in which the first and second regions are annular bands having a width of about 0.25 mm to about 2.0 mm.

* * * * *